(12) United States Patent
Hoshiya

(10) Patent No.: US 7,366,644 B2
(45) Date of Patent: Apr. 29, 2008

(54) METHOD OF JUDGING PRACTICAL CONDITIONS FOR USE OF AN ORDERED ALLOY UNDER IRRADIATION ENVIRONMENTS

(75) Inventor: Taiji Hoshiya, Higashi-Ibaraki-gun (JP)

(73) Assignee: Japan Nuclear Cycle Development Institute, Ibaraki-ken (JP)

( * ) Notice: Subject to any disclaimer, the term of this patent is extended or adjusted under 35 U.S.C. 154(b) by 341 days.

(21) Appl. No.: 10/995,142

(22) Filed: Nov. 24, 2004

(65) Prior Publication Data

US 2005/0125205 A1 Jun. 9, 2005

(30) Foreign Application Priority Data

Dec. 5, 2003 (JP) .............................. 2003-408026

(51) Int. Cl.
*G06F 7/60* (2006.01)
*G06F 17/10* (2006.01)
*G21G 1/00* (2006.01)

(52) U.S. Cl. ......................................... 703/2; 376/156
(58) Field of Classification Search .................... 703/2, 703/5, 6; 376/156, 157, 158
See application file for complete search history.

(56) References Cited

U.S. PATENT DOCUMENTS 5,307,385 A * 4/1994 Shimanuki et al. ......... 376/249

OTHER PUBLICATIONS

Hoshiya et al., Modeling of neutron irradiation response for B2-type ordered alloys, Aug. 1, 2004, Journal of Nuclear Materials, vols. 329-333, Part 2, pp. 1043-1047.*

Hishinuma, A., Radiation damage of TiAl intermetallic alloys, Dec. 1, 1996, Journal of Nuclear Materials, vol. 239, pp. 267-272.*

Dunlop et al., Search for damage and/or disordering effects due to intense electronic excitation in crystalline metallic alloys irradiated by high-energy heavy ions, Feb. 19, 1990, Journal of Physics: Condensed Matter, vol. 2, pp. 1733-1741.*

Report 1: Shuichi Iwata et al., "Materials Data Base for Fusion Reactors-I", Journal of Nuclear Materials, vol. 103 (1982), pp. 173-177.

(Continued)

*Primary Examiner*—Ngoc-Yen Vu
*Assistant Examiner*—James A Meyers
(74) *Attorney, Agent, or Firm*—Wenderoth, Lind & Ponack, L.L.P.

(57) ABSTRACT

An irradiated state diagram that expresses a relation of a degree of long range order S to a variable R of an irradiated state related to a damage rate and an irradiation temperature is prepared according to an ordered structure of an alloy on basis of an evaluation formula related to an effect of irradiation on an irradiated state of the alloy by using, as parameters, a first threshold value $S_{th1}$ at which the degree of long range order begins to decrease greatly under irradiation, a second threshold value $S_{th2}$ at which the degree of long range order substantially reaches equilibrium after this decrease, and a degree of long range order in an equilibrium state $S_{eq}$. An R-value is calculated and an S-value corresponding to the R-value is found. An $S_{th1}$-value, an $S_{th2}$-value and an $S_{eq}$-value at the R-value are found and compared.

8 Claims, 1 Drawing Sheet

OTHER PUBLICATIONS

Report 2: Hajime Nakajima et al., "Present status of Data-Free-Way—Distributed database for advanced nuclear materials", Journal of Nuclear Materials, vol. 212/215 (1994), pp. 1711-1714.

Report 3: Mitsutane Fujita et al., "Application of the distributed database (Data-Free-Way) on the analysis of mechanical properties in neutron irradiated 316 stainless steel", Fusion Engineering and Design, vol. 51/52 (2000), pp. 769-774.

Report 4: Yoshiyuki Kaji et al., "Status of JAERI Material Performance Database (JMPD) and Analysis of Irradiation Assisted Stress Corrosion Cracking (IASCC) Data", Journal of Nuclear Science and Technology, vol. 37 (2000), pp. 949-958.

* cited by examiner

US 7,366,644 B2

METHOD OF JUDGING PRACTICAL CONDITIONS FOR USE OF AN ORDERED ALLOY UNDER IRRADIATION ENVIRONMENTS

FIELD OF THE INVENTION

The present invention relates to a method of judging practical conditions for use of an ordered alloy (in this specification, "alloy" is used as a term including an alloy and an intermetallic compound) having an ordered structure in irradiation environments. This technique is useful for deriving practical conditions for use of elemental equipment or structures formed from ordered alloys in environments in which materials used are exposed to radiation having high energy, for example, in the nuclear technology field including reactors and accelerators and in the space technology field.

BACKGROUND OF THE INVENTION

In using new materials in irradiation environments in which high-energy corpuscular beams are emitted and occurrence of severe irradiation damage is expected, it is necessary to evaluate beforehand usability and long-period soundness of materials in these environments. Hence, in prior art, an irradiation test plan in which environments are simulated is first formulated, irradiation experiments in which many irradiation conditions are parameterized are conducted, and obtained systematic post-irradiation examination (PIE) data is analyzed to thereby obtain practical conditions in which materials can be used under irradiation.

However, in order to conduct a high-accuracy evaluation analysis that can ensure high safety and reliability during use of materials, a long period and much cost for an enormous number of tests and a sufficient analysis are required. For example, in development of materials for fission reactors in study of light-water reactors and high-temperature gas reactors, and development of materials for nuclear fusion reactors, in a case where new materials that have no irradiation result are used in irradiation environments, development of new materials represented by Zircaloy, HASTELLOY XR (an Ni—Mo—Cr(Fe) based alloy), austenitic stainless steels, fine-grained isotropic graphite, and the like has required a development period on the order of 10 years and an enormous development cost has been indispensable.

Therefore, as described in the following Reports 1-4, there have been available methods by which multiple research institutes store enormous irradiation data in collaboration by assembling an irradiation database on materials and use this data in analyses. Under present circumstances, however, such methods have not yet reached a stage at which irradiation data can be systematically analyzed, and there is no analysis solution, calculation code or data base capable of easily deriving practical conditions for use.

A description of irradiation damage to materials is very complex. Irradiation damage starts with collision of high-energy particles and is composed of instantaneous heating and cooling processes and various reaction processes, such as atomic displacement, generation, growth and diffusion of defects, aggregation and coalescence of defects, and initiation and propagation of cracks. Although part of these reactions are expressed by mathematical formulae such as a diffusion equation, almost all of these reactions require high-speed and large-capacity processing by a computer on the basis of statistical processing by molecular dynamics, the Monte Carlo method and dislocation dynamics. For this reason, because at present there is a limit to calculating performance of computers, it is difficult to analyze an entire picture of irradiation damage and to systematically grasp the irradiation damage even if a next-generation super computer is used. Furthermore, there is no evaluation formula that enables a description of irradiation damage to be reflected in an evaluation of material characteristics and, therefore, it has hitherto been impossible to instantaneously derive practical conditions under which materials can be used under irradiation (practical conditions for use).

A problem to be solved by the present invention is that in pursuing application of new materials represented by ordered alloys subjected to irradiation environments, there is no method of judging practical conditions for use of the materials under irradiation in a short period and at low cost and that for this reason, it has been difficult to introduce materials that have no irradiation result.

Report 1: Shuichi Iwata et al., Materials Data Base for Fusion Reactors-1, Journal of Nuclear Materials, Vol. 103 (1982), pp. 173-177.

Report 2: Hajime Nakajima et al., Present status of Data-Free-Way—Distributed database for advanced nuclear materials, Journal of Nuclear Materials, Vol. 212/215 (1994), pp. 1711-1714.

Report 3: Mitsutane Fujita et al., Application of the distributed database (Data-Free-Way) on the analysis of mechanical properties in neutron irradiated 316 stainless steel, Fusion Engineering and Design, Vol. 51/52 (2000), pp. 769-774.

Report 4: Yoshiyuki Kaji et al., Status of JAERI Material Performance Database (JMPD) and Analysis of Irradiation Assisted Stress Corrosion Cracking (IASCC) Data, Journal of Nuclear Science and Technology, Vol. 37 (2000), pp. 949-958.

SUMMARY OF THE INVENTION

According to the present invention, there is provided a method by which irradiation behavior is assumed to be caused by generation and annihilation of irradiation defects, an index that expresses an irradiated state is used, an evaluation formula in which an effect of irradiation environments on the index is considered is derived on the basis of the index, and changes in the index due to the effect of irradiation and conditions of the irradiation environments on that occasion are simply and rapidly predicted.

More specifically, according to the present invention there is provided a method of judging practical conditions for use of an ordered alloy in irradiation environments, comprising steps of: preparing an irradiated state diagram that expresses a relation of a degree of long range order S to a variable R of an irradiated state related to a damage rate, which can be obtained from fluence rate, and an irradiation temperature on basis of an evaluation formula related to an effect of irradiation on an irradiated state of an alloy according to an ordered structure of the alloy by using, as parameters, a first threshold value $S_{th1}$ at which the degree of long range order begins to decrease greatly under irradiation, a second threshold value $S_{th2}$ at which the degree of long range order substantially reaches equilibrium after this decrease, and a degree of long range order in an equilibrium state $S_{eq}$; calculating an R-value of an irradiated state under irradiation conditions under which an alloy to be judged is to be used and finding an S-value of degree of long range order corresponding to the R-value; and finding and comparing an $S_{th1}$-value, an $S_{th2}$-value and an $S_{eq}$-value at the R-value, to thereby predict a damage level and a variation condition of the damage level and judge practical conditions for use.

Also, according to the present invention there is provided a method of judging practical conditions for use of an ordered alloy in irradiation environments, comprising steps of: preparing an irradiated state diagram that expresses a relation of a damage rate (fluence rate) to a reciprocal of an irradiation temperature on basis of an evaluation formula related to an effect of irradiation on an irradiated state of an alloy according to an ordered structure of the alloy by using, as parameters, a first threshold value $S_{th1}$ at which the degree of long range order begins to decrease greatly under irradiation, a second threshold value $S_{th2}$ at which the degree of long range order substantially reaches equilibrium after this decrease, and a degree of long range order in an equilibrium state $S_{eq}$; calculating a value of the reciprocal of an irradiation temperature of an alloy to be judged under irradiation conditions under which the alloy is to be used, and finding an S-value of degree of long range order corresponding to the value of the reciprocal of the irradiation temperature; and finding and comparing an $S_{th1}$-value, an $S_{th2}$-value and an $S_{eq}$-value at the value of the reciprocal of the irradiation temperature, to thereby predict a damage level and a variation condition of the damage level and judge practical conditions for use.

In these judgment methods, a comparison is made between the S-value and the $S_{th1}$-value, the $S_{th2}$-value and the $S_{eq}$-value, respectively, at the same R-value or the same value of the reciprocal of an irradiation temperature (where, $0 \leq S_{eq} < S_{th2} < S_{th1} < 1$), and from a magnitude relation of these values judgments can be made as follows:

(1) When $S_{th1}$-value<S-value: the alloy to be judged is in an ordered state and has a low damage level (the degree of long range order is large);

(2) When $S_{th2}$-value<S-value<$S_{th1}$-value: the alloy to be judged is in a transition process from an ordered state to a disordered state and its damage level fluctuates greatly and tends to increase rapidly (the degree of long range order decreases substantially);

(3) When $S_{eq}$-value<S-value<$S_{th2}$-value: the alloy to be judged is in a process of substantially reaching a disordered state and its damage level is large but fluctuates little (the amount of a decrease in the degree of long range order is small and the degree of long range order is small) and;

(4) When S-value<$S_{eq}$-value: the alloy to be judged is in a disordered state and has a high damage level (the degree of long range order is small).

According to the present invention, it is possible to substantially simplify a large number of irradiation experiments that have hitherto been necessary and to simply and rapidly derive practical conditions for use of an ordered alloy (an alloy with an ordered structure) under irradiation, such as irradiation temperature, damage rate (fluence rate) and irradiation fluence, without need for assembling a new irradiation database. For this reason, it is possible to substantially shorten periods of enormous irradiation tests, post-irradiation examinations (PIE) and analysis evaluations, long-period implementation of which has hitherto been indispensable, and it is possible to radically reduce prior-irradiation test expenses, irradiation test expenses, post-irradiation examination expenses, analysis expenses, and the like. As a result of this, it is possible to rapidly and efficiently promote development of new materials that are resistant to irradiation environments, such as an ordered alloy.

DETAILED DESCRIPTION OF THE PREFERRED EMBODIMENTS

Figure 1:
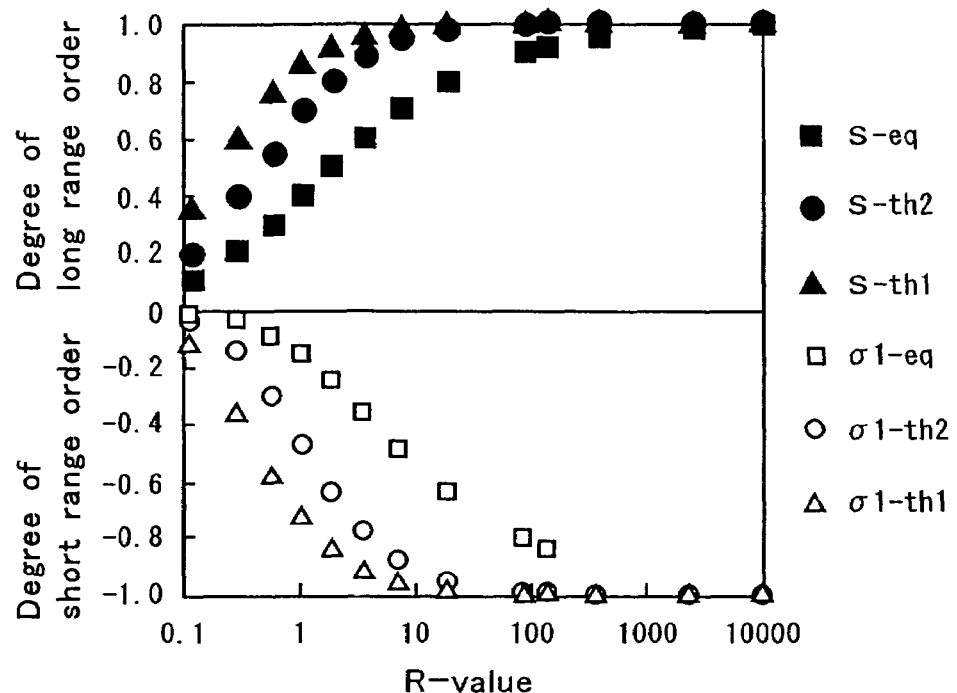
FIG. 1 is a relation diagram of degree of long range order (degree of short range order) and R-value of a B2-type ordered alloy.

In the present invention, an evaluation formula based on order-disorder transition under irradiation is used. Atomic replacement generated by irradiation induces a local structural change in an ordered alloy, and the ordered alloy is disordered under irradiation. On the other hand, introduction of irradiation defects is promoted with an irradiation temperature and ordering of the ordered alloy is promoted. An irradiated state of the ordered alloy is a process in which such disordering and ordering proceed simultaneously, and under conditions in which disordering and ordering are balanced, this irradiated state is greatly influenced by variations in irradiation temperature, damage rate (fluence rate) and irradiation fluence that constitute irradiation environmental conditions.

Hence, by paying attention to a degree of long range order of an ordered alloy as an index that expresses an irradiated state that reflects an effect of irradiation, an influence of irradiation on a degree of long range order is analyzed and an evaluation formula in which the effect of irradiation on the degree of long range order is considered is derived. "The degree of order" used herein is a physical quantity that expresses a kind of atomistic quantity having order and a degree of this order in an order-disorder transition, and this is a parameter that features phase transition. A relationship between an irradiation temperature and a damage rate corresponding to a threshold value of the effect of irradiation is found by this evaluation equation and a diagram for analysis of an irradiated state is prepared. When this diagram for each ordered alloy is prepared, conditions of damage rate and irradiation temperature that can be used under irradiation become apparent easily.

Typically, an irradiated state diagram that expresses a relation of a degree of long range order S to a variable R of an irradiated state related to a damage rate and an irradiation temperature is prepared according to an ordered structure of an alloy on basis of an evaluation formula related to the effect of irradiation on an irradiated state of the alloy by using, as parameters, a first threshold value $S_{th1}$ at which the degree of long range order begins to decrease greatly under irradiation, a second threshold value $S_{th2}$ at which the degree of long range order substantially reaches equilibrium after this decrease, and the degree of long range order in an equilibrium state $S_{eq}$. On the other hand, an R-value of an irradiated state under irradiation conditions under which an alloy to be judged is to be used is calculated and an S-value of degree of long range order corresponding to the R-value is found. At the same time, an $S_{th1}$-value, an $S_{th2}$-value and an $S_{eq}$-value at the R-value are found and compared.

A comparison is made between the S-value and the $S_{th1}$-value, the $S_{th2}$-value and the $S_{eq}$-value, respectively, at the same R-value (where, $0 \leq S_{eq}$-value<$S_{th2}$-value<$S_{th1}$-value<1), and from a magnitude relation of these values judgments can be made as follows:

(1) When $S_{th1}$-value<S-value: the alloy is in an ordered state and has a low damage level (the degree of long range order is large);

(2) When $S_{th2}$-value<S-value<$S_{th1}$-value: the alloy is in a transition process from an ordered state to a disordered state and its damage level fluctuates greatly and tends to increase rapidly (the degree of long range order decreases substantially);

(3) When $S_{eq}$-value<S-value<$S_{th2}$-value: the alloy is in a process of substantially reaching a disordered state and its damage level is large but fluctuates little (an amount of a decrease in the degree of long range order is small and the degree of long range order is small) and;

(4) When S-value<$S_{eq}$-value: the alloy is in a disordered state and has a high damage level (the degree of long range order is small).

In this manner, a damage level and a variation condition of the damage level are predicted and practical conditions for use are judged.

When considering the following Example, the following is to be taken into consideration:

1) "dpa/s" is an abbreviation for displacement per second, and is also referred to as displacement speed and displacement rate. It represents the amount of displacement of constituting atoms per unit time (1 second). 1 dpa/s means that all constituting atoms are displaced once in one second, and represents that all the constituting atoms (100%) are displaced and that 100% defects are produced.

2) "CsCl" denotes a cesium-chlorine type ordered structure alloy. Specifically, it represents an ordered structure alloy of a body-centered cubic type, and denotes an ordered structure alloy having a chlorine atom (Cl), or a cesium atom (Cs), at the center (body center) of a unit cubic lattice, and cesium atoms (Cs), or chlorine atoms (Cl), at the eight positions of the unit cubic lattice which surround the atom located at the center.

3) "B2-type" denotes a crystal structural type in which a composition ratio of the number of A atoms to the number of B atoms is 1:1, with the A atoms and B atoms constituting a binary alloy. "B2-type" is a generic term used to refer to a cesium-chlorine type ordered structure alloy.

EXAMPLE

An irradiated state depends greatly on irradiation temperature, irradiation damage and damage rate that constitute irradiation environments. Damage rates under irradiation conditions in Japan Materials Testing Reactor (JMTR) of Japan Atomic Energy Research Institute are $10^{-7}$ to $10^{-8}$ dpa/s and damage rates under irradiation conditions in Experimental Fast Reactor (JOYO) of Japan Nuclear Cycle Development Institute are $10^{-6}$ to $10^{-8}$ dpa/s. Temperatures at which damage of an ordered alloy irradiated in these testing reactors is recovered are derived by making a comparison between irradiation environmental conditions and threshold values in an irradiated state diagram according to the present invention, and an irradiated state can be judged on the basis of the temperatures.

Derivation of an evaluation formula related to an irradiation effect is performed as follows. A case of a B2-type ordered alloy (a CsCl-type ordered alloy, a composition ratio of a number of A atoms to a number of B atoms is 1:1, A atoms and B atoms constituting a binary alloy), which is a representative ordered alloy, is illustrated here by an example. However, also cases of other ordered alloys can be similarly handled. The same applies also when a degree of short range order by Warren-Cowley or the like is used in place of the degree of long range order (a degree of long range order of Bragg-Williams). The degree of long range order (the degree of long range order of Bragg-Williams) S of a B2-type ordered alloy under irradiation is defined by S=(the probability that composed sublattices are correctly occupied by constituent atoms)−(the probability that composed sublattices are not correctly occupied by constituent atoms). That is, $$S = \frac{C_A^\alpha - C_A}{1 - C_A} = \frac{C_B^\beta - C_B}{1 - C_B}$$

$$(0 \leq S \leq 1, C_A + C_B = 1)$$

where, $\alpha$ and $\beta$ denote an $\alpha$ sublattice and a $\beta$ sublattice, respectively, in the ordered alloy and subscripts A and B denote an A atom and a B atom, respectively. The rate of time change of this degree of long range order is given by:

$$\frac{dS}{dt} = \left[\frac{dS}{dt}\right]_{disordering} + \left[\frac{dS}{dt}\right]_{ordering}$$

$$= -\varepsilon\phi S + K(1-S)^2$$

where, the former term of the right side denotes a disordering rate and the latter term denotes an ordering rate.

In the present specification, symbols in formulae are as follows:

$\varepsilon$: Efficiency of disordering $\phi$: Damage rate

K: Function of temperature $$K = (Z_\alpha + Z_\beta - 2)c_v \cdot v \cdot c_A c_B \exp\left(-\frac{E}{kT}\right)$$

$Z_\alpha$, $Z_\beta$: Coordination number of $\alpha$ sublattices and $\beta$ sublattices Cv: Vacancy concentration (assumed to be proportional to the 1/2-th power of the damage rate)

v: Frequency factor $C_A$, $C_B$: Concentration of A atoms and B atoms

E: Activation energy for the ordering jump of vacancy $\kappa$: Boltzmann constant T: Temperature The following equation is obtained from balance conditions of the ordering process and disordering process in irradiation environments:

$$\frac{dS}{dt} = -\varepsilon\phi\{S - R(1-S)^2\} = \varepsilon\phi R(S-\alpha)(S-\beta) = 0$$

where, the two roots of $\alpha$ and $\beta$ are given by:

$$\alpha, \beta = \frac{2R+1}{2R} \pm \sqrt{\frac{4R+1}{4R^2}}$$

(A plus or minus sign should be chosen in the double sign, $\beta<\alpha$, $0<\beta<1$, $1<\alpha$)

A solution is obtained only for $S=\beta$ that satisfies $0 \leq S<1$.

However, $R=\kappa/\epsilon\phi=S_{eq}/(1-S_{eq})^2$ ($0 \leq R<\infty$)

where, $S_{eq}$ denotes the degree of long range order in an equilibrium state.

Therefore, the following analytic solution using R as a parameter is obtained:

$$S = \beta + \frac{(\alpha-\beta)(1-\beta)}{(\alpha-1)\exp\{\epsilon R(\alpha-\beta)\phi t\}+(1-\beta)} \quad \text{(Equation 1)}$$

The degree of long range order S decreases gradually from a value before irradiation (S=1) with increasing irradiation time due to irradiation and reaches an equilibrium value in a certain irradiation time. The former term β in the equation is the degree of long range order in an equilibrium state $S_{eq}$ corresponding to a convergent value at this time. The latter term is a time dependent term and shows details of time variations in the degree of long range order that gradually approximates the degree of long range order in an equilibrium state with increasing irradiation time.

A relationship between the first threshold value $S_{th1}$ at which the degree of long range order S begins to decrease greatly under irradiation, the second threshold value $S_{th2}$ at which the degree of long range order substantially reaches equilibrium after this decrease, and the parameter R is given by the following equations from results of secondary differential and primary differential related to R:

$$S_{th1} = 1 + \frac{1}{2R}\left\{1 - \frac{(4R+1)^2}{(2R+1)(4R+1)+4R^2}\right\} \quad \text{(Equation 2)}$$

$$= 1 + \frac{\epsilon\phi}{2K}\left\{1 - \frac{(4K+\epsilon\phi)^2}{(2K+\epsilon\phi)\cdot(4K+\epsilon\phi)+4K^2}\right\}$$

$$S_{th2} = \frac{2R}{2R+1} = \frac{2K}{2K+\epsilon\phi} \quad \text{(Equation 3)}$$

Furthermore, the degree of long range order in an equilibrium state $S_{eq}$ is found by the following equation:

$$S_{eq} = 1 + \frac{1}{2R}\left\{1 - (4R+1)^{\frac{1}{2}}\right\} \quad \text{(Equation 4)}$$

$$= 1 + \frac{(\epsilon\phi)^{\frac{1}{2}}}{2K}\left\{(\epsilon\phi)^{\frac{1}{2}} - (4K+\epsilon\phi)^{\frac{1}{2}}\right\}$$

$$= \frac{1}{2K}\left[2K + \epsilon\phi - \{\epsilon\phi(4K+\epsilon\phi)\}^{\frac{1}{2}}\right]$$

where, $0 \leq S_{eq} < S_{th2} < S_{th1} < 1$.

On the other hand, degrees of short range order of Warren-Cowley σ corresponding to each of the degrees of long range order are found as follows. The number of A-A atom pairs formed by A atoms in a binary alloy with its nearest neighbor atom is given by:

$$N_{AA} = (1/2)N \cdot Z \cdot C_A \cdot P_{AA}$$

$P_{AA}$: The probability that an A atom in an α sublattice and an A atom in a β sublattice that constitute the alloy form A-A atom pairs.

Z: Coordination number $P_{AA}$ is approximated as follows:

$$p_A^i = \begin{cases} 1, & i \in \alpha \\ 0, & i \in \beta \end{cases}$$

$$p_A^j = \begin{cases} 1, & j \in \beta \\ 0, & j \in \alpha \end{cases}$$

$(i = 1, 2, \ldots, N \cdot c_A, j = 1, 2, \ldots, N \cdot (1-c_A))$ $p_A^i (i \in \alpha)$, $p_A^j (j \in \beta)$: The proportion at which A atoms occupy α and β sublattice points $$P_{AA} = \frac{\frac{1}{2}N}{\frac{1}{2}N \cdot c_A \cdot Z} \sum_{i \neq j} p_A^i p_A^j \quad (i \in \alpha, j \in \beta)$$

$$= \frac{1}{Z \cdot c_A} \sum_{i \neq j} p_A^i p_A^j$$

However, it is assumed that in nearest neighboring atoms, there is no correlation between an A-A atom pair formed by A atoms within the same sublattice ($\epsilon_{AA}=0$). Calculation conditions related to the summation of the subscripts of the above equation are as follows:

$$\begin{cases} \sum_{\alpha,\beta} p_A^k = p_A^\alpha + p_A^\beta = 1 & (k=\alpha, \beta) \\ \sum_i p_A^i = N_\alpha \cong N_A = N \cdot c_A & (i=1, 2, \ldots, N \cdot c_A, i \in \alpha) \\ \sum_i p_A^j = N_\beta \cong N_B = N \cdot (1-c_A) & (j=1, 2, \ldots, N \cdot (1-c_A), \\ & j \in \beta, i \neq j) \\ \sum_l N_l = N_A + N_B = N & (l=\alpha, \beta) \end{cases}$$

On the other hand, a relationship with the degree of long range order S is expressed by the following equation:

$$S = \frac{p_A^\alpha - c_A}{1 - v} = \frac{p_A^\alpha - c_A}{\gamma}$$

However, from the relationship between $C_A$ and v (relative concentration of α sublattice), the value of γ is given by:

$\gamma = C_A(1-v)/v$ when $C_A \leq v$ $\gamma = 1 - C_A$ when $C_A \geq v$

From these relationships the following equation stands:

$p_A^\alpha = S \cdot \gamma + c_A$

In the case of a B2-type ordered alloy, from the condition that $Z_\alpha=Z_\beta=Z$, the following equation is obtained:

$$p_{AA} = \frac{1}{Zc_A}[\{c_A Z_\alpha + (1-c_A)Z_\beta\}(c_A + \gamma \cdot S) \times (1 - c_A - \gamma \cdot S)]$$

$$= \frac{1}{c_A}(c_A + \gamma \cdot S) \times (1 - c_A - \gamma \cdot S)$$

$$p_{AA} = c_A - \frac{\gamma^2 S^2}{c_A}$$

From the definition, the degree of short range order $\sigma_1$ holds:

$$\sigma_1 = 1 - \frac{p_{AB}}{c_B} = 1 - \frac{p_{BA}}{c_A} = 1 - \frac{1-p_{BB}}{c_A} = 1 - \frac{1-p_{AA}}{c_B}$$

$$\text{where } \begin{cases} p_{AA} + p_{AB} = 1 \\ p_{BA} + p_{BB} = 1 \\ c_A p_{AB} = c_B p_{BA} \end{cases}$$

Therefore, from $\sigma_1=(P_{AA}-C_A)/C_B$, the following equation is obtained:

$$\sigma_1 = -\gamma^2 S^2/C_A(1-C_A) \qquad \text{(Equation 5)}$$

According to the present invention, the degree of long range order (degree of short range order) is calculated by substituting an R-value found from irradiation conditions and the degree of long range order in an equilibrium state, and it is possible to predict an irradiated state from the value of the degree of long range order (degree of short range order). A relationship between the degree of long range order (degree of short range order) and the R-value (an irradiated state diagram) is shown in FIG. 1. Because the R-value is a function of damage rate $\phi$ and K-value (R=K/$\epsilon\phi$) and the K-value is a function of irradiation temperature T, it follows that the R-value becomes a function of damage rate $\phi$ and irradiation temperature T. The upper half of FIG. 1 shows, as a function of R, the first threshold value $S_{th1}$ at which the degree of long range order begins to decrease greatly under irradiation, which is found from Equation 2, the second threshold value $S_{th2}$ at which the degree of long range order substantially reaches equilibrium after this decrease, which is found from Equation 3, and the degree of long range order in an equilibrium state $S_{eq}$, which is found from Equation 4. The lower half of FIG. 1 shows degrees of short range order by Equation 5 from each of the degrees of long range order.

A judgment method using the irradiated state diagram of FIG. 1 is as follows. An R-value is calculated from a specific irradiation condition related to a new material to be used and an S-value of the degree of long range order found from Equation 1 is described within FIG. 1. A comparison is made between the S-value and an $S_{th1}$-value, an $S_{th2}$-value and an $S_{eq}$-value, respectively, at the same R-value (where, $0 \leq S_{eq}$-value<$S_{th2}$-value<$S_{th1}$-value<1), and from a magnitude relation of these values judgments are made in a qualitative manner as follows:

(1) When $S_{th1}$-value<S-value: the new material to be used is in an ordered state and has a low damage level (the degree of long range order is large);

(2) When $S_{th2}$-value<S-value<$S_{th1}$-value: the new material is in a transition process from an ordered state to a disordered state and its damage level fluctuates greatly and tends to increase rapidly (the degree of long range order decreases substantially);

(3) When $S_{eq}$-value<S-value<$S_{th2}$-value: the new material is in a process of substantially reaching a disordered state and its damage level is large but fluctuates little (the amount of a decrease in the degree of long range order is small and the degree of long range order is small) and;

(4) When S-value<$S_{eq}$-value: the new material is in a disordered state and has a high damage level (the degree of long range order is small).

Also, from the degree of short range order in FIG. 1 it is possible to judge local information, such as a tendency of a pair of dissimilar atoms ($\sigma$: a negative value) or a pair of atoms of the same kind ($\sigma$: a positive value) relating to nearest neighboring atoms.

As shown in FIG. 1, curves related to the degree of long range order and the degree of short range order spread greatly vertically and it is expected that in a material in which the degree of order comes very close to ±1, deterioration in properties under irradiation is small. In FIG. 1, various irradiation conditions are converted to an R-value that is simple and changes predicted with respect to the degree of order are made visible via the R-value (as a function of the R-value), thereby making it possible to spatially grasp behavior of these changes. As a result of this, it becomes easy to make a comparison with various changes in physical properties and relations to these can be easily found.

Table 1 shows a relationship between the threshold values of the degree of long range order and those of the degree of short range order.

| Degree of long range order of Bragg-Williams S | | | Degree of short range order of Warren-Cowley $\sigma_1$ (between the nearest neighbor atoms) | | |
|---|---|---|---|---|---|
| Equilibrium value | Threshold value | | Equilibrium value | Threshold value | |
| $S_{eq}$ | $S_{th2}$ | $S_{th1}$ | $\sigma_{1-eq}$ | $\sigma_{1-th2}$ | $\sigma_{1-th1}$ |
| 0.1 | 0.197 | 0.351 | −0.01 | −0.039 | −0.123 |
| 0.2 | 0.385 | 0.598 | −0.04 | −0.148 | −0.358 |
| 0.3 | 0.550 | 0.757 | −0.09 | −0.303 | −0.573 |
| 0.4 | 0.690 | 0.857 | −0.16 | −0.476 | −0.734 |
| 0.5 | 0.800 | 0.918 | −0.25 | −0.64 | −0.843 |
| 0.6 | 0.882 | 0.956 | −0.66 | −0.778 | −0.914 |
| 0.7 | 0.940 | 0.979 | −0.49 | −0.884 | −0.958 |
| 0.8 | 0.976 | 0.992 | −0.64 | −0.953 | −0.984 |
| 0.9 | 0.994 | 0.998 | −0.81 | −0.988 | −0.996 |
| 0.92 | 0.997 | 0.999 | −0.846 | −0.994 | −0.998 |
| 0.95 | 0.999 | 0.999 | −0.998 | −0.998 | −0.998 |
| 0.98 | 0.999 | 0.999 | −0.998 | −0.998 | −0.998 |
| 0.99 | 0.999 | 0.999 | −0.998 | −0.998 | −0.998 |

The R-value (R=K/$\epsilon\phi$=$S_{eq}$/(1−$S_{eq}$)$^2$: (0≦R<∞)) is found by determining the $S_{eq}$-value, and if the R-value is determined, the $S_{th1}$-value and the $S_{th2}$-value are found from Equations 2 and 3, since each of $S_{th1}$- and $S_{th2}$-values is a function of the R-value. On the other hand, the degree of short range order is found from an obtained degree of long range order by using Equation 5, and $\sigma_{eq}$-value, $\sigma_{th1}$-value and $\sigma_{th2}$-value are obtained from the $S_{eq}$-value, the $S_{th1}$-value and the $S_{th2}$-value, respectively. Table 1 shows results obtained in this manner.

From the results of Table 1, it is apparent that in a case where an equilibrium value of the degree of long range order is close to 0.1 to 0.2, for example, (which corresponds to a state in which disordering is remarkable), an extent to which the degree of order begins to lower, $S_{th1}$, begins to decrease abruptly from 0.6, almost approaches equilibrium at 0.39 or so and reaches 0.2 (equilibrium value). Also, when the degree of order begins to decrease from 0.35 or so, $S_{th1}$ substantially approaches equilibrium at 0.2, and reaches equilibrium at 0.1. If this degree of order that begins to lower, $S_{th1}$, has large values of 0.9 to 0.8 or so, then a decrease in the degree of order can be suppressed to 0.8 (equilibrium value: 0.5) to 0.6 (equilibrium value: a little less than 0.4) even if the degree of order decreases (disordering does not occur). In contrast, if the $S_{th1}$-value becomes not more than 0.6, the degree of long range order decreases abruptly and it follows that disordering becomes remarkable.

In response to these changes, the degree of short range order is obtained by squaring the degree of long range order, multiplying this value by a coefficient, and reversing the symbol of the value. Therefore, in a case where an equilibrium value of the degree of long range order is close to 0.1 to 0.2, an equilibrium value of the short range order shows −0.01 to −0.04 and becomes a value that is substantially close to zero (disordering). On the other hand, in a case where an equilibrium value of the degree of long range order is close to 0.9 to 0.8, an equilibrium value of the short range order is −0.8 to −0.6 and this shows that ordering of short range order (ordering of pairs of dissimilar atoms) has proceeded even at an atomic level.

As to a difference between the degree of long range order and the degree of short range order, the degree to which the degree of order lowers is larger in the degree of short range order than in the degree of long range order, and this suggests that even when a decrease in the degree of order at a long range order level is small in the degree of long range order, there may be a case where a decrease in the degree of short range order has proceeded more when viewed in terms of a change in the degree of short range order at an atomic level.

The degree of short range order is a degree of order within a range of an atomic level of a first neighboring atom, a second neighboring atom and a third neighboring atom, i.e., within the nearest atom, the nearest neighboring atom second to this nearest atom, and the nearest neighboring atom next to this next neighboring atom (in Table 1, only cases between the nearest neighboring atoms are shown). In contrast, the degree of long range order corresponds to a degree of order within a relatively large range from several to tens of crystal lattices, and not an atomic level. The relationship shown by Equation 5 exists between both degrees of order. In Equation 5, the degree of short range order is obtained by multiplying a square of the degree of long range order by a constant and reversing the symbol of this value. By way of example, when the degree of long range order approaches 1, the degree of short range order approaches −1 (pairs of dissimilar atoms).

The relationship between the degree of short range order and the degree of long range order is as follows. In terms of the degree of long range order, the closer to 1 the value, the larger the extent of ordering, whereas the closer to 0 the value, the higher the extent of disordering. In terms of the degree of short range order, ordering of dissimilar atoms occurs when the value is close to −1 and ordering of atoms of the same kind occurs when the value is close to +1, whereas disordering occurs when the value is close to 0.

When an actual process of irradiation damage is considered, irradiation damage occurs first to an extent that high-energy particles (neutrons, ions, electrons, and the like) collide against a material, thereby producing irradiation defects of fine level (a level of the degree of short range order), these irradiation defects then grow and coalesce, forming large aggregates of defects (a level of the degree of long range order) and finally leading to cracks and breakages. The degree of short range order is more than an auxiliary judgment material and indispensable for making judgments at a fine level in an initial stage of a damage process. In actual cases, after judgment on a damage state of an entire sample by use of the degree of long range order, a local damage state is verified by the degree of short range order. In this sense, it is appropriate to consider that the degree of short range order is used in making judgments in a "complementary" manner rather than in an "auxiliary" manner.

A relationship between temperature T and damage rate (damage speed) $\phi$ is given by the following equation:

$$-\frac{E}{kT} - \frac{1}{2}\ln\phi = \ln R + \ln\frac{\varepsilon(zv)^{\frac{1}{2}}}{(Z_\alpha + Z_\beta - 2)\cdot C_A C_B}$$

The relationship between damage rate (damage speed) and temperature when the degree of long range order reaches equilibrium is as follows:

$$\ln\phi_{eq} = -\frac{2E}{kT_{eq}} - 2\left[\ln R + \ln\left\{\frac{\varepsilon(zv)^{\frac{1}{2}}}{(Z_\alpha + Z_\beta - 2)C_A C_B}\right\}\right]$$

$$= -\frac{2E}{kT_{eq}} - 2\ln\frac{R\cdot\varepsilon(zv)^{\frac{1}{2}}}{(Z_\alpha + Z_\beta - 2)C_A C_B}$$

where, $T_{eq}$ denotes a temperature at which the degree of long range order reaches equilibrium. Similarly, the following equation is obtained:

$$\ln\phi_{th2} = -\frac{2E}{kT_{th2}} - 2\ln\frac{\varepsilon(zv)^{\frac{1}{2}}}{(Z_\alpha + Z_\beta - 2)C_A C_B} - 2\ln\frac{S_{th2}}{2(1 - S_{th2})}$$

$$\ln\phi_{th1} = -\frac{2E}{kT_{th1}} - 2\ln\frac{\varepsilon(zv)^{\frac{1}{2}}}{(Z_\alpha + Z_\beta - 2)C_A C_B} - 2\ln\frac{(4 - 3S_{th1}^2)^{\frac{1}{2}} + 3S_{th1} - 2}{12(1 - S_{th1})}$$

where, $T_{th1}$- and $T_{th2}$-values and $\phi_{th1}$- and $\phi_{th2}$-values denote, respectively, threshold-value temperatures and threshold-value damage rates related to the degree of long range order.

Figure 2:
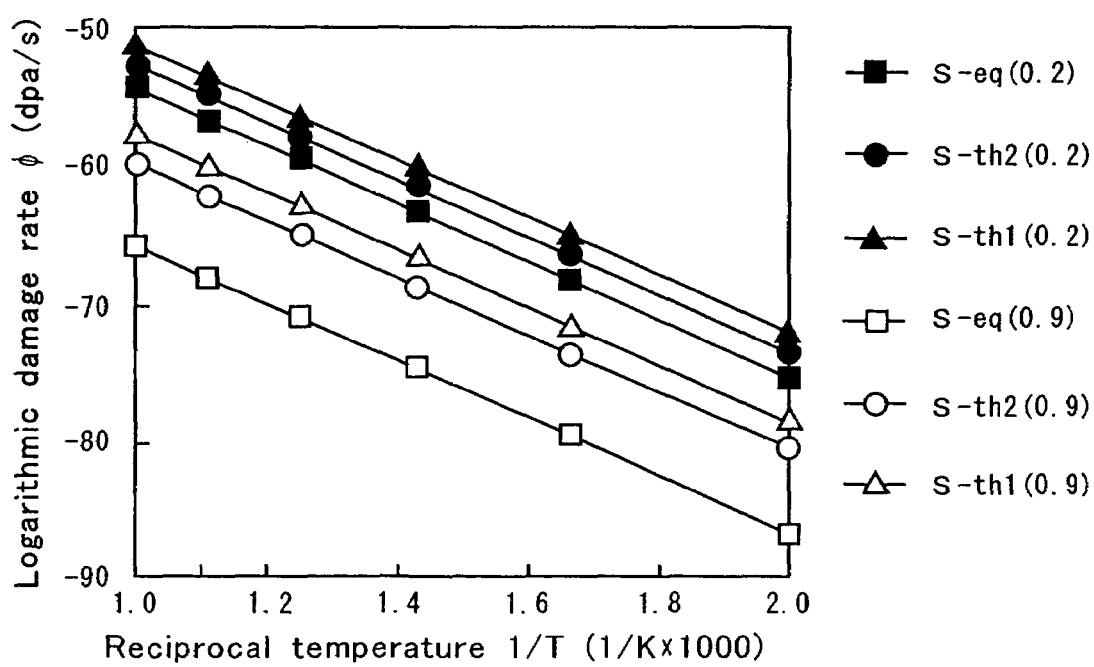
FIG. 2 is a relation diagram of damage rate and irradiation temperature of a B2-type ordered alloy.

FIG. 2 shows how to make judgments directly from irradiation conditions, and it shows a relationship between a logarithmic damage rate, which is an actual irradiation condition, and a reciprocal of irradiation temperature. Because the same equations as in FIG. 1 are used, the degree of long range order S to be found is unique and the method of FIG. 1 and the method of FIG. 2 are equivalent to each other in calculating the S-value. Although the degree of short range order shown in FIG. 1 is not shown in FIG. 2, a similar diagram is obtained by describing the degree of short range order found by using Equation 5 in the drawing in the same manner as in FIG. 1, if necessary.

FIG. 2 provides convenience in that the S-value can be judged directly from actual irradiation conditions without calculation of the R-value. In this case, in predicting changes in the S-value, deciphering work and the like are not easy compared to FIG. 1, because a spatial image related to prediction of the S-value is not directly obtained and besides a logarithmic representation is used. However, judgments can be easily made if one becomes skillful in line drawing work related to the diagram and deciphering work. Incidentally, the straight lines in FIG. 2 tend to move to down left in the figure when a recovery from damage is made and they tend to move to top right when damage proceeds.

EXEMPLIFICATION

The present inventors conducted a neutron irradiation test related to a TiNi alloy, which is a B2-type ordered alloy, in Japan Materials Testing Reactor (JMTR) of Japan Atomic Energy Research Institute. From results of this test, it became apparent that when changes in the degree of long range order are evaluated from changes in an amount of decrease in transition temperature found from electric resistance measurement, a decrease in the degree of long range order by irradiation with neutrons can be suppressed by holding the irradiation temperature at a level exceeding 520 K, thereby greatly improving deterioration in properties by irradiation, and that the method of the present invention is valid also experimentally.

According to the present invention that uses an irradiated state diagram thus devised, it is possible to substantially shorten periods of enormous irradiation tests, post-irradiation examinations and analysis evaluations, long-period implementation of which has hitherto been indispensable, and to simply and rapidly derive practical conditions for use of an ordered alloy under irradiation. According to the present invention, in developing new materials that usually require developmental periods of not less than 10 years, it is possible to shorten the periods to not more than several years, i.e., to not more than ⅓ the periods that have hitherto been required, and the present inventors could have the prospect that development of materials that withstand irradiation environments is possible at low cost.

What is claimed is:

1. A method of judging practical conditions for use of an ordered structure alloy under an irradiation environment, comprising:

preparing an irradiated state diagram that expresses for the ordered structure alloy a relation of a degree of long range order S to a variable R of an irradiated state of the ordered structure alloy, related to a damage rate and an irradiation temperature, on basis of an evaluation formula related to an effect of irradiation on the degree of long range order of the ordered structure alloy under irradiation environments by using as parameters, a first threshold value $S_{th1}$ at which the degree of long range order begins to decrease, under irradiation, at a rate greater than a rate at which the degree of long range order decreased prior to the first threshold value having been reached, a second threshold value $S_{th2}$ at which the degree of long range order is nearer to reaching equilibrium than the degree of long range order was prior to the second threshold value having been reached and after decrease of the degree of the long range order which began at the first threshold value $S_{th1}$, and the degree of long range order in an equilibrium state $S_{eq}$;

for irradiation conditions under which the ordered structure alloy is to be used, calculating an R-value, and corresponding to the R-value, finding an S-value, an $S_{th1}$-value, an $S_{th2}$-value, and an $S_{eq}$-value; and comparing the S-value, the $S_{th1}$-value, the $S_{th2}$-value, and the $S_{eq}$-value, to thereby predict a damage level and a variation condition of the damage level of the ordered structure alloy under the irradiation environment.

2. The method according to claim 1, wherein
comparing the S-value, the $S_{th1}$-value, the $S_{th2}$-value, and the $S_{eq}$-value, with $0<S_{eq}$-value$<S_{th2}$-value$<S_{th1}$-value$<1$, and considering a magnitude relation of these values, results in the following judgments being made (i) when $S_{th1}$-value$<$S-value, the ordered structure alloy is in an ordered state and has a large degree of long range order, corresponding to a low damage level, (ii) when $S_{th2}$-value$<$S-value$<S_{th1}$-value, the ordered structure alloy is in a transition process from an ordered state to a disordered state and the degree of long range order decreases, corresponding to a damage level of the alloy fluctuating greatly and tending to increase rapidly, (iii) when $S_{eq}$-value$<$S-value$<S_{th2}$-value, the ordered structure alloy is in a process of reaching a disordered state and an amount of a decrease in the degree of long range order is small while the degree of long range order is small, corresponding to a damage level of the alloy being large but fluctuating little, and (iv) when S-value$<S_{eq}$-value, the ordered structure alloy is in a disordered state and the degree of long range order is small, corresponding to a high damage level.

3. The method according to claim 2, wherein
the degree of long range order S is equal to the probability that composed sublattices are correctly occupied by constituent atoms minus the probability that that composed sublattices are not correctly occupied by constituent atoms.

4. The method according to claim 1, wherein
the degree of long range order S is equal to the probability that composed sublattices are correctly occupied by constituent atoms minus the probability that that composed sublattices are not correctly occupied by constituent atoms.

5. A method of judging practical conditions for use of an ordered structure alloy under an irradiation environment, comprising:

preparing an irradiated state diagram that expresses for the ordered structure alloy a relation of a damage rate to a reciprocal of an irradiation temperature on basis of an evaluation formula, related to an effect of irradiation on a degree of long range order S of the ordered structure alloy under irradiation environments, by using as parameters, a first threshold value $S_{th1}$ at which the degree of long range order begins to decrease, under irradiation, at a rate greater than a rate at which the degree of long range order decreased prior to the first threshold value having been reached, a second threshold value $S_{th2}$ at which the degree of long range order is nearer to reaching equilibrium than the degree of long range order was prior to the second threshold value having been reached and after decrease of the degree of the long range order which began at the first threshold value $S_{th1}$, and the degree of long range order in an equilibrium state $S_{eq}$;

for irradiation conditions under which the ordered structure alloy is to be used, calculating a value of the reciprocal of an irradiation temperature of the ordered structure alloy, and corresponding to the value of the reciprocal of the irradiation temperature, finding an S-value, an $S_{th1}$-value, an $S_{th2}$-value, and an $S_{eq}$-value; and comparing the S-value, the $S_{th1}$-value, the $S_{th2}$-value, and the $S_{eq}$-value, to thereby predict a damage level and a variation condition of the damage level of the ordered structure alloy under the irradiation environment.

6. The method according to claim 5, wherein comparing the S-value, the $S_{th1}$-value, the $S_{th2}$-value, and the $S_{eq}$-value, with $0 < S_{eq}$-value$< S_{th2}$-value$< S_{th1}$-value$< 1$, and considering a magnitude relation of these values, results in the following judgments being made (i) when $S_{th1}$-value$<$S-value, the ordered structure alloy is in an ordered state and has a large degree of long range order, corresponding to a low damage level, (ii) when $S_{th2}$-value$<$S-value$<S_{th1}$-value, the ordered structure alloy is in a transition process from an ordered state to a disordered state and the degree of long range order decreases, corresponding to a damage level of the alloy fluctuating greatly and tending to increase rapidly, (iii) when $S_{eq}$-value$<$S-value$<S_{th2}$-value, the ordered structure alloy is in a process of reaching a disordered state and an amount of a decrease in the degree of long range order is small while the degree of long range order is small, corresponding to a damage level of the alloy being large but fluctuating little, and (iv) when S-value$<S_{eq}$-value, the ordered structure alloy is in a disordered state and the degree of long range order is small, corresponding to a high damage level.

7. The method according to claim 6, wherein the degree of long range order S is equal to the probability that composed sublattices are correctly occupied by constituent atoms minus the probability that that composed sublattices are not correctly occupied by constituent atoms.

8. The method according to claim 5, wherein the degree of long range order S is equal to the probability that composed sublattices are correctly occupied by constituent atoms minus the probability that that composed sublattices are not correctly occupied by constituent atoms.

* * * * *